United States Patent [19]

Koo

[11] Patent Number: 5,780,723
[45] Date of Patent: Jul. 14, 1998

[54] SEALING QUALITY TESTER AND ITS CONTROL METHOD FOR A CAR

[75] Inventor: Ja-Hoi Koo, Kyoungki-do, Rep. of Korea

[73] Assignee: Kia Motors Corporation, Seoul, Rep. of Korea; a part interest

[21] Appl. No.: 591,428

[22] Filed: Jan. 19, 1996

[30] Foreign Application Priority Data

Sep. 19, 1995 [KR] Rep. of Korea ............... 1995-30795

[51] Int. Cl.[6] ..................................................... G01N 29/02
[52] U.S. Cl. ...................... 73/40.5 A; 73/632; 340/425.5
[58] Field of Search .................... 73/40, 46, 40.5 A, 73/632, 602; 340/605, 438, 425.5; 364/508; 381/44

[56] References Cited

U.S. PATENT DOCUMENTS

| | | | |
|---|---|---|---|
| 4,100,808 | 7/1978 | Evans | 73/612 |
| 5,331,855 | 7/1994 | Takashita | 73/602 |
| 5,432,755 | 7/1995 | Komninos | 367/135 |
| 5,476,010 | 12/1995 | Fleming | 73/620 |

*Primary Examiner*—Christine K. Oda

[57] ABSTRACT

A sealing quality tester and a control method therefor includes an ultrasonic transmitter, a power supply, a charging detector, an ultrasonic oscillator and an ultrasonic generator; and an ultrasonic receiver. The ultrasonic receiver includes an ultrasonic signal detector, an A/D converting unit, a controller, a power supply, a key input unit, a sound generator and a liquid crystal display.

1 Claim, 9 Drawing Sheets

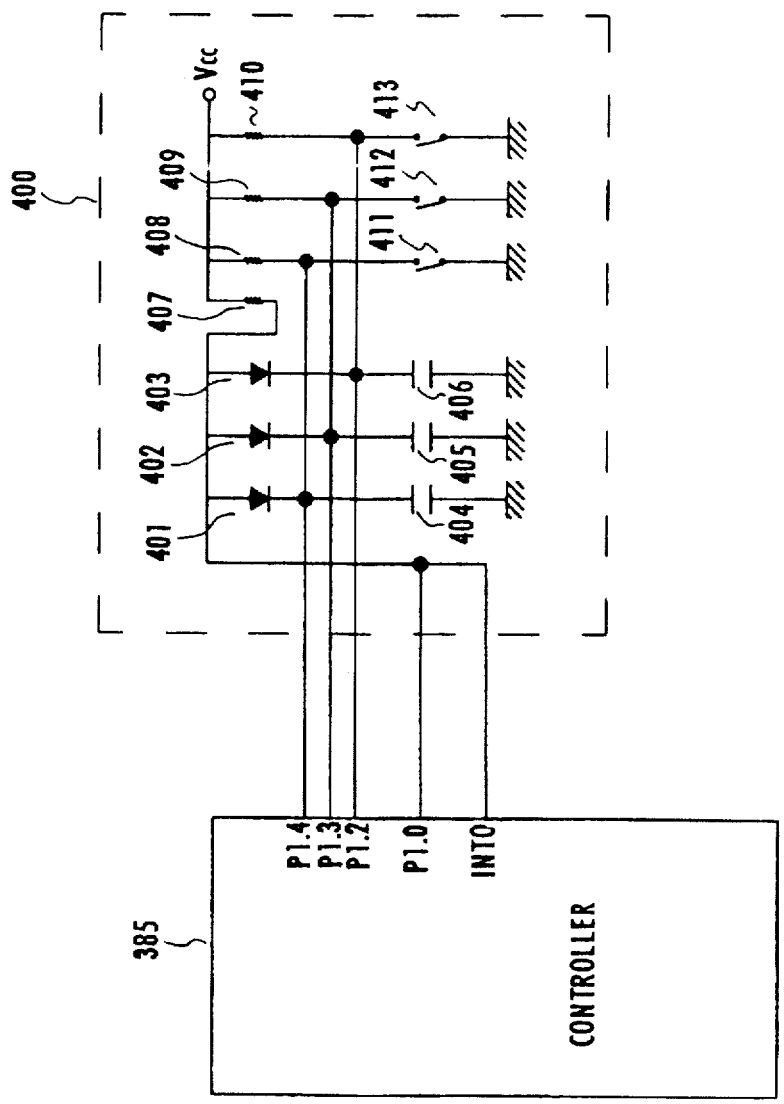

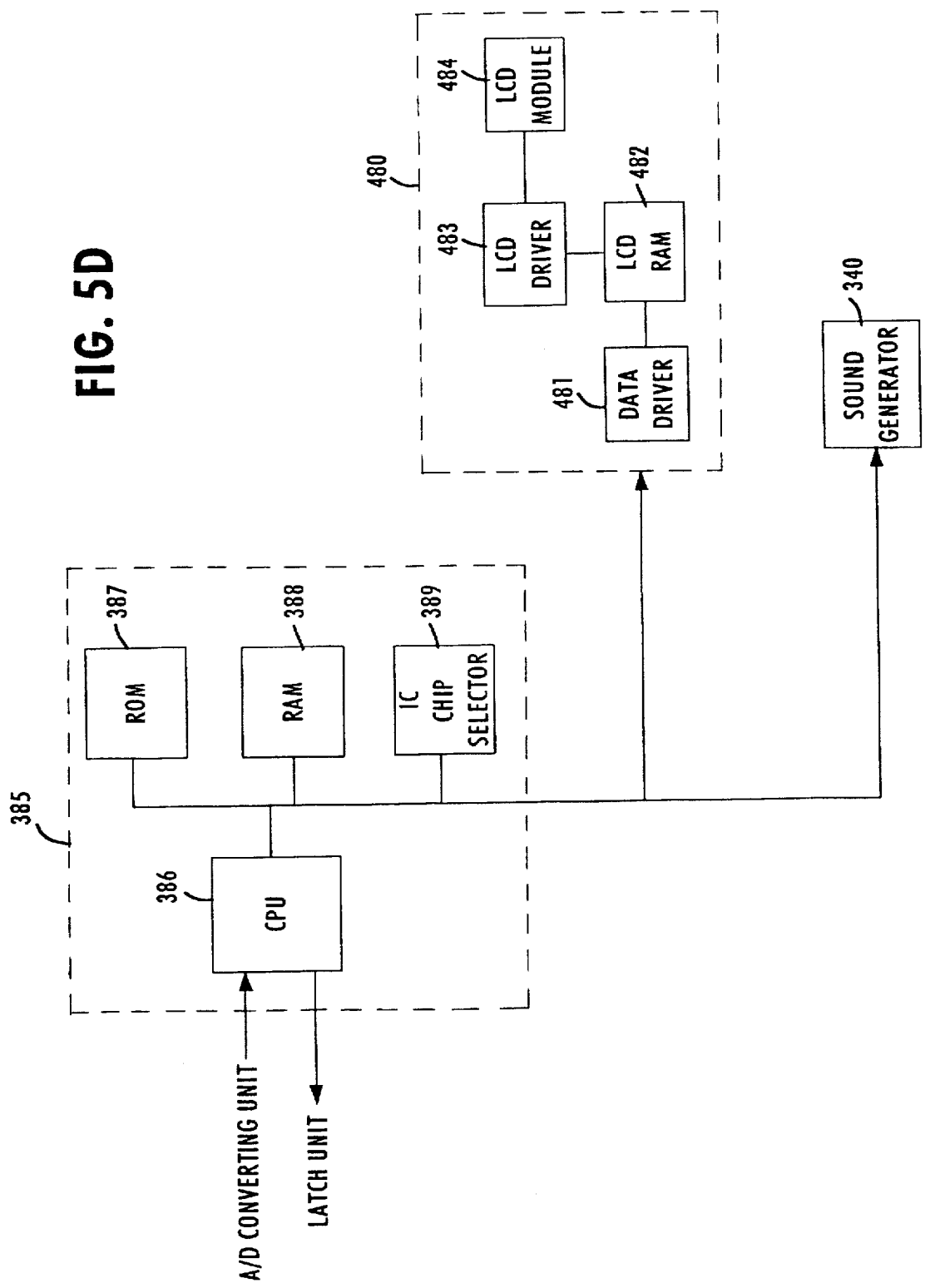

SEALING QUALITY TESTER AND ITS CONTROL METHOD FOR A CAR

FIELD OF INVENTION

This invention refers to a sealing quality tester for a car and a control method therefor, in particular to the sealing quality tester and its control method for the car using an ultrasonic generator.

PRIOR ART

In general, a car is constructed with numerous mechanical and electronic components. It is necessary that these components should be combined with each other with precision so that no unwanted holes or chasms be formed at their contact surfaces in the car.

Thus, in the assembling process of the car, the sealing quality of the completely constructed car is tested in order to find out that there are any holes or chasms formed in the car.

The sealing quality is mainly tested at the contact surfaces of the components such as the front glass window, the rear glass window, trunk, the rear hatch, the door's weather strip and so forth.

In prior art, the conventional methods for testing sealing quality include the smoke test and the shower test. They are executed as follows:

Firstly, in the smoke test, the car is sealed up by closing the components such as the door and windows, and then a sufficient smoke or compressed air are injected into the inside of the sealed car.

Thereafter, the contact surfaces, where the sealing quality is suspicious, are inspected by an examiner with the naked eye.

Secondly, in the shower test, water is sprayed on the sealed car for the determined amount of time, and the car is then visually inspected by the examiner with the naked eye on whether water has penetrated the inside of the car.

But in these conventional methods of testing the sealing quality of the car, the following problems occur:

Damage is inflicted on the inside of the car by the smell of smoke or by the water used in the sealing quality test. This damage occurs because the completely constructed car is tested using physical means such as smoke or water. In addition, any minute holes or chasms formed in the car cannot be found by the naked eye of the examiner.

Furthermore, in the prior art, the shower tester and the smoke generator used in the sealing quality test require an excess amount of space to install them and usually require 2 hours to 24 hours to implement said test.

Also, in a case where a repaired car has any errors such as water leakage, even an experienced engineer cannot quickly and easily find the location of the fault in the sealing quality. Thus, correcting or repairing the fault becomes very time consuming and in the process, greatly increases the cost of repair.

SUMMARY OF THE INVENTION

Thus, the object of this invention is to solve the problems mentioned in the prior art and in particular, to provide a sealing quality tester and its controlling method using an ultrasonic transceiver so that even the inexperienced inspector can easily detect very fine holes or chasms formed in the inside of the car without disassembling it.

The sealing quality tester of the car of this invention to achieve said object includes: an ultrasonic transmitting means comprising of: a power supply, a charging detector, an ultrasonic oscillator and an ultrasonic generator; and an ultrasonic receiving means comprising of an ultrasonic receiver, an ultrasonic signal detector, A/D converting unit, controller, a power supply, a key input unit, a sound generator and a liquid crystal display.

Also, the controlling method of the sealing quality tester of the car of this invention includes: the up or down switch selecting step to regulate the multiplying ratio and the sensitivity of the ultrasonic signals received in the ultrasonic signal receiver; the manual/fuzzy mode selecting step to regulate the multiplying ratio and the sensitivity of the ultrasonic signals received in the ultrasonic signal receiver according to the selecting of the up or down switch in the up or down switch selecting step manually or fuzzily; the multiplying ratio and the sensitivity increasing step to increase the multiplying ratio and the sensitivity of the ultrasonic signals received in the ultrasonic signal receiver according to the selecting of the up switch in the up or down switch selecting step; the multiplying ratio and the sensitivity decreasing step to decrease the multiplying ratio and the sensitivity of the ultrasonic signals received in the ultrasonic signal receiver according to the selecting of the down switch in the up or down switch selecting step; and the displaying step to display the multiplying ratio and the sensitivity regulated signal according to the selecting of the up or down switch in the up or down switch selecting step on the LCD and the sound generator.

BRIEF DESCRIPTIONS OF THE DRAWINGS

The above object and other advantages of the present invention will become more apparent by describing in detail the preferred embodiment of the present invention with reference to the attached drawings, in which:

FIG. 5C is a detailed circuit diagram showing a part of the ultrasonic receiving means of the invention.

FIG. 5D is a block diagram showing the composition of the controller and the LCD.

DETAILED DESCRIPTION OF THE PREFERRED EMBODIMENT

The following is in reference to the preferred embodiments of the present invention shown in FIG. 1 to FIG. 6, wherein similar elements are designated with identical numerals throughout the several views.

Figure 1:
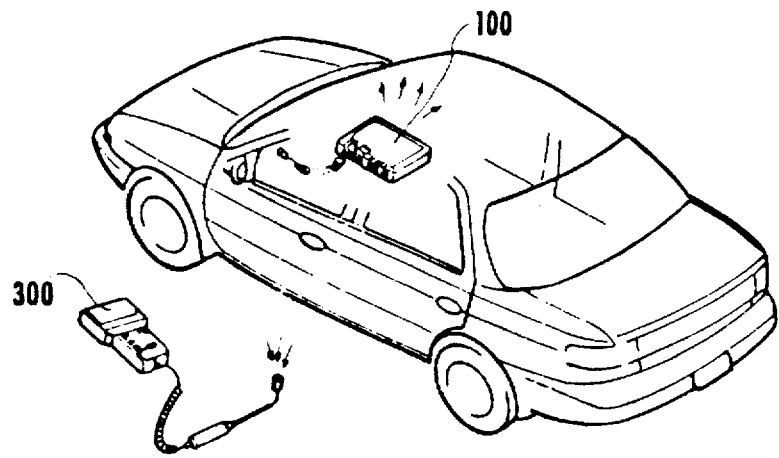
FIG. 1 is a perspective view showing the installed state of the sealing quality tester in the car.
Figure 2:
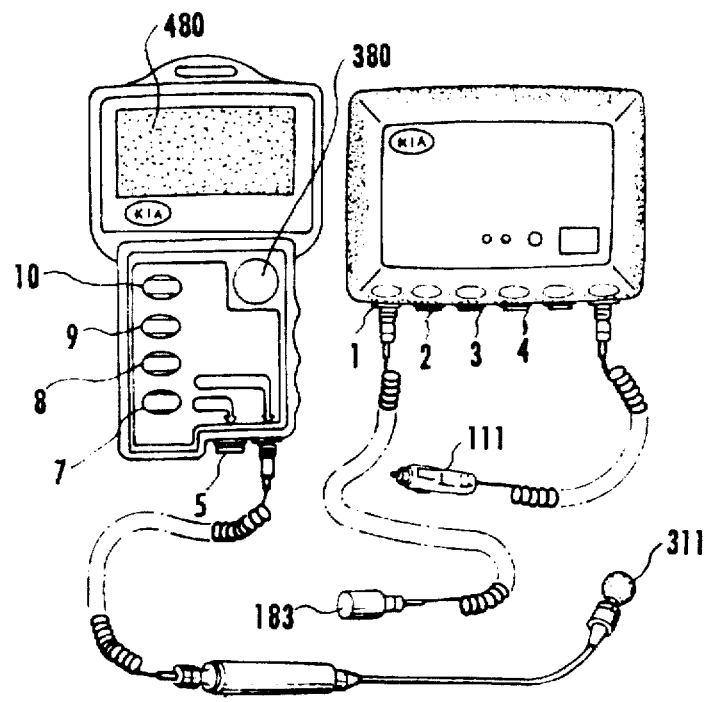
FIG. 2 is a perspective view showing the ultrasonic transmitting means and the ultrasonic receiving means of the sealing quality tester of the car of the invention.
Figure 3:
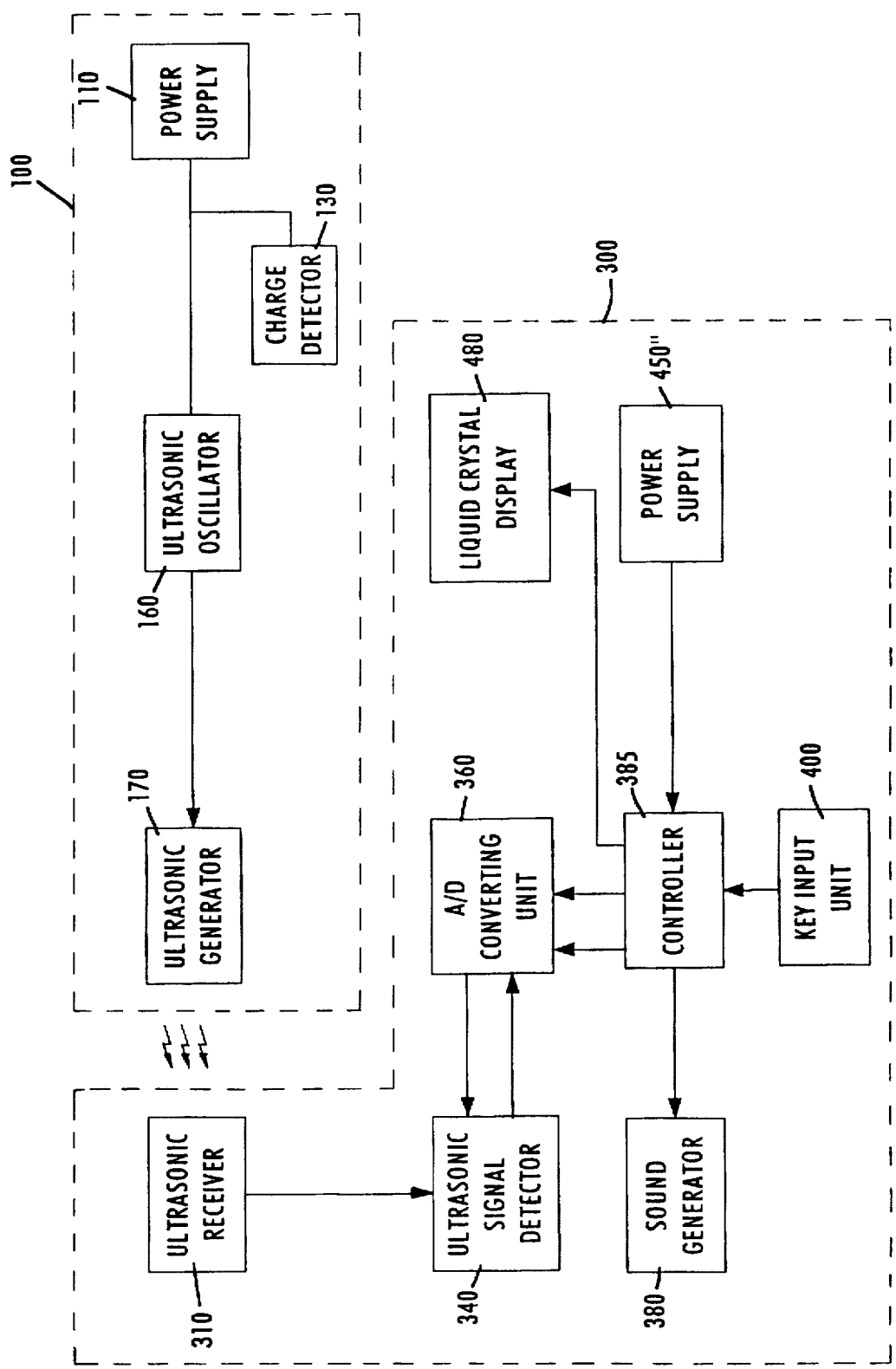
FIG. 3 is a block diagram showing the composition of the ultrasonic transmitting means and the ultrasonic receiving means of the sealing quality tester.

Firstly, as shown in FIG. 3, the sealing quality tester of the preferred embodiment of the invention comprises an ultrasonic transmitting means 100 comprising a power supply 110, a charge detector 130 for a supplementary power supply, an ultrasonic oscillator 160 and an ultrasonic generator 170; and an ultrasonic receiving means 300 comprising of an ultrasonic receiver 310, an ultrasonic signal detector 340, an A/D converting unit 360, controller 385, a power supply 450, a key input unit 400, a sound generator 380 and a liquid crystal display 480.

Figure 4:
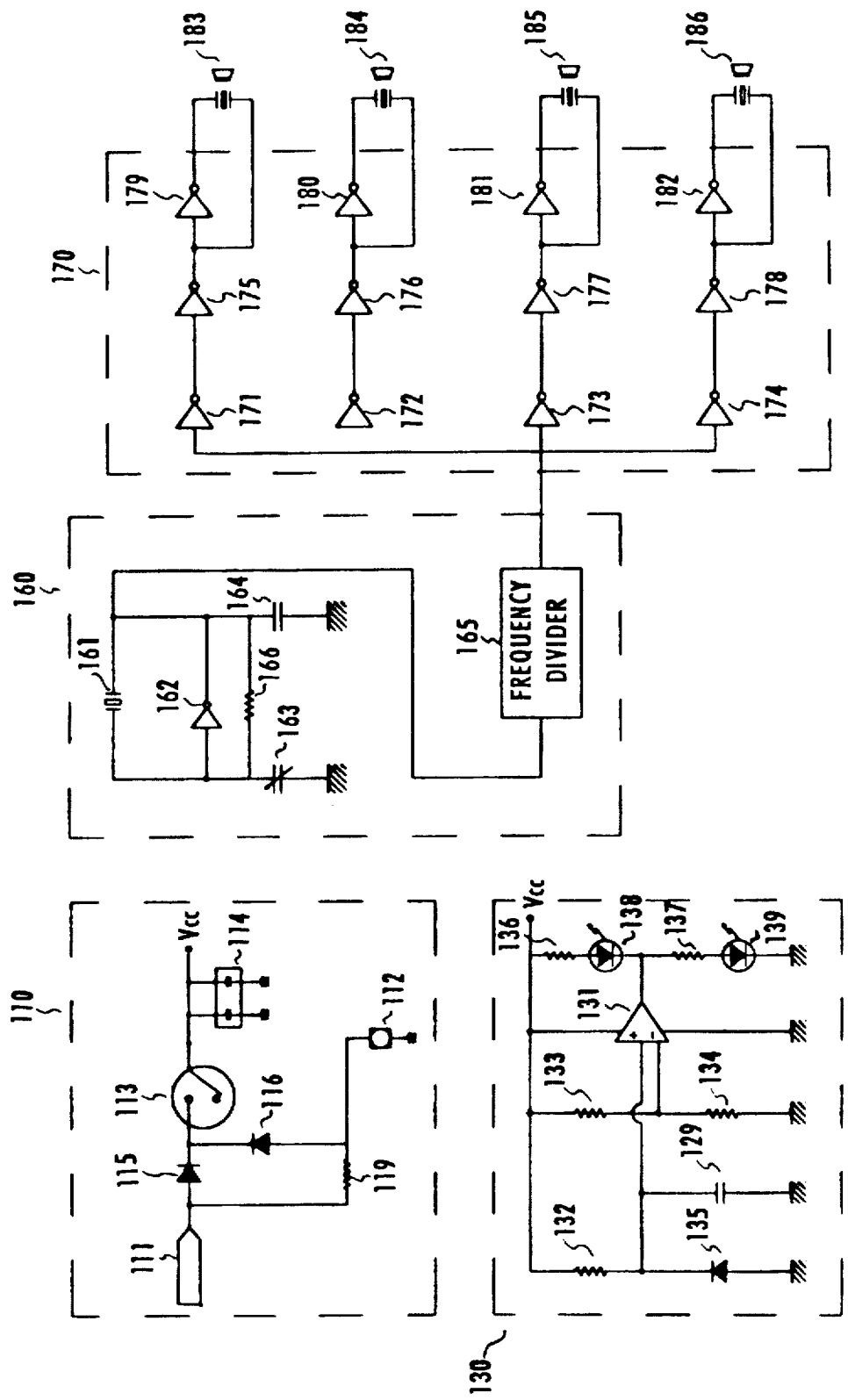
FIG. 4 is a detailed circuit diagram showing for the ultrasonic transmitting means of the sealing quality detector of the invention.

The power supply 110, as shown in FIG. 4, of the ultrasonic transmitting means 100, includes: a battery 111; a power switch 113; a supplementary power supply 112 charged by the battery 111; plural capacitors 114 which block noise components introduced through electric wires in the car and stabilize a reference voltage(Vcc); diodes 115, 116 which block the reverse flow of the current; and a resistor 119 which drops the applied voltage from battery 111 to a supplementary power supply 112.

Also, the charge detector 130 in the ultrasonic transmitting means 100, as shown in FIG. 4, includes: voltage dividing resistors 133, 134 which drop the reference voltage (Vcc) applied from the power supply 110; a zener diode 135; a voltage dividing resistor 132 which drops the reference voltage(Vcc) and apply the dropped voltage of the reference voltage to the zener diode 135; a capacitor 129 which stabilizes the zener voltage of the zener diode 135; a comparator 131 wherein the zener voltage of the zener diode 135 is applied to its noninverting terminal and the dropped voltage of the Vcc by the voltage dividing resistor 133, 134 is applied to its inverting terminal; the first LED(light emitting diode) 138 which emits light when the output of the comparator 131 is high or low; the second LED 139 which emits light when the output of the comparator 131 is high; and voltage dividing resistor 136, 137 which drop the voltage applied to the first and second LED 138, 139.

Also, the ultrasonic oscillator 160, as shown in FIG. 4, of the ultrasonic transmitting means 100, includes: a crystal oscillator 161 which oscillates by 4 MHz when the voltage is applied to both ends of its electrode; CMOS invertor 162 which amplifies the reference voltage and applies the applied reference voltage to the crystal oscillator 161; a feedback resistor 166 which feedbacks the output voltage of the CMOS invertor 162 and stabilizes the voltage applied to the crystal oscillator 161 to the desired extent; a variable capacitor 163 which regulates the oscillation frequency from the crystal oscillator 161; a blocking capacitor 164 which blocks the harmonic components oscillated from the crystal oscillator 161; and a frequency divider 165 which divides the oscillation frequency of the signal from the crystal oscillator 161 by a hundredth ratio.

Also, the ultrasonic generator 170, as shown in FIG. 4, of the ultrasonic transmitting means 100, includes: CMOS invertors 171–174 which buffer the oscillation signal applied from the frequency divider 165; ultrasonic generation sensors 183–186; and invertors 175–182 in which each pair of CMOS invertor, such as 171 and 175, is connected serially and thus, the inverted output signals from each CMOS invertor 171–174 are applied to one terminal of the ultrasonic generation sensor 183–186 and the noninverted output signals from each CMOS invertor 171–174 are applied to the other terminal of the ultrasonic generation sensors 183–186.

Figure 5A:
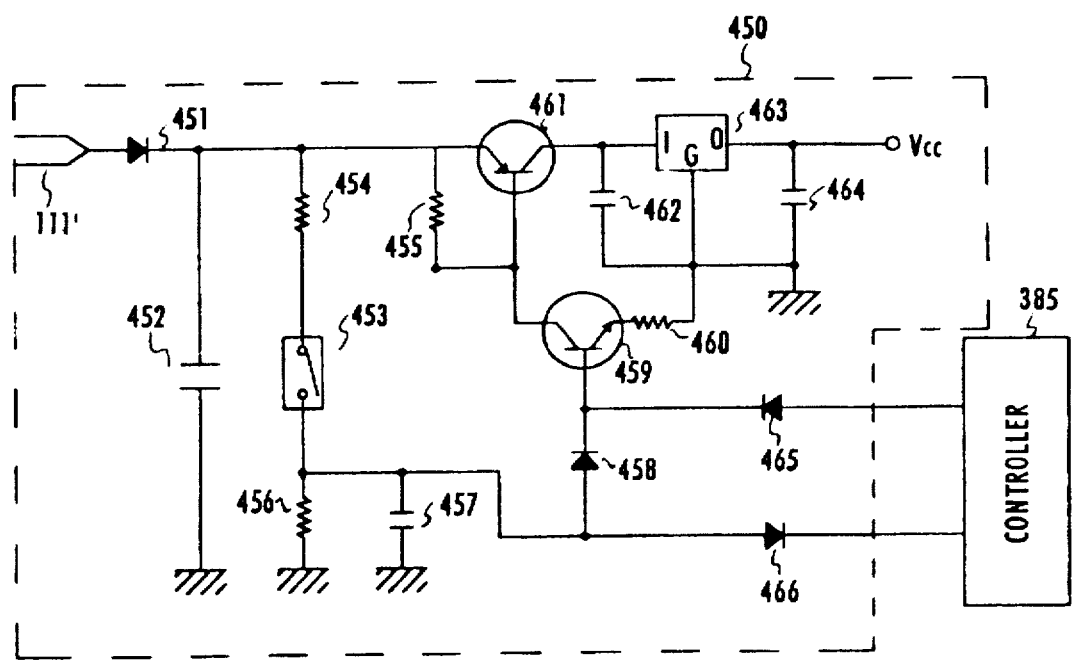
FIG. 5A is a detailed circuit diagram showing of a part of the ultrasonic receiving means of the invention.

In regards to the power supply 450, as shown in FIG. 5A, of the ultrasonic receiving means 300, includes: a diode 451 conducting the power of the battery; a capacitor 452 which stabilizes the voltage through the diode 451; voltage dividing resistors 454, 456 which drop the voltage passing through the diode 451; a power switch 453 which is placed between the voltage dividing resistors 454 and 456; a capacitor 457 which stabilizes the voltage applied to the resistor 456; the first base common transistor 461 which becomes on when a low signal is applied to its base; the second base common transistor 459 in which its collect is connected to the base of the first base common transistor 461; and a electrostatic voltage IC 463 in which the collector of the first base common transistor 461 is connected to its input terminal.

Figure 5B:
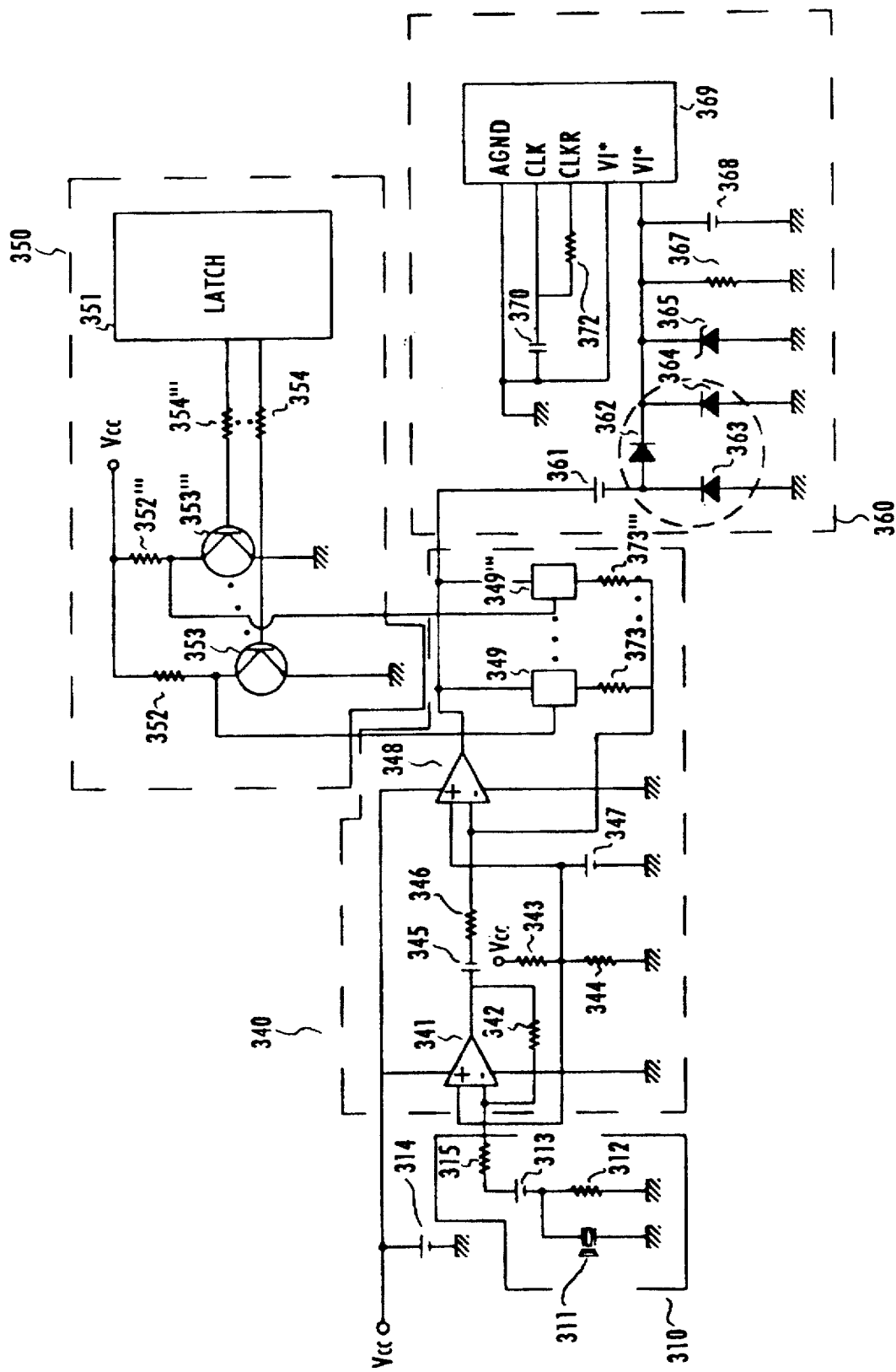
FIG. 5B is a detailed circuit diagram showing a part of the ultrasonic receiving means of the invention.

Also, the ultrasonic receiver 310, as shown in FIG. 5B, of the ultrasonic receiving means 300, includes: a ultrasonic receiving sensor 311; a resistor 312 for matching the impedance of the ultrasonic receiving sensor 311; and a high pass filter 314 which consists of a capacitor 313 and a resistor 315 and passes through high-pass band signals outputted from the ultrasonic receiving sensor 311.

Also, a received signal detector 340, as shown in FIG. 5B, of the ultrasonic receiving means 300, includes: voltage dividing resistors 343, 344 which drop the reference voltage (Vcc) ; a capacitor 344 which stabilizes the voltage of the resistor 344; the first OP-AMP 341 in which the output signal of the ultrasonic receiver 310 is inputted to its inverting terminal and the dropped voltage of the reference voltage(Vcc) by the resistor 343, 344 is inputted to its noninverting terminal and thus, the difference voltage of the two terminals is amplified by the ratio of the resistance of the resistor 342 and 315; a capacitor 345 which blocks the DC component of the output signal of the first OP-AMP 341; the second OP-AMP 348 in which the output of the first OP-AMP 341 is inputted to the inverting terminal and the voltage of the resistor 344 is inputted to the noninverting terminal and thus, the difference voltage of the two terminals is amplified by the ratio of the resistance of the resistors 373 and 346; and a analog switch 349. At this time, the number of the analog switch 349 and resistor 373 are plural.

Also, the latch unit 350, as shown in FIG. 5B, of the ultrasonic receiving means 300, includes: a latch 351 which stores the amplifying level controlling signal for the received ultrasonic signal transiently and outputs the signal selectively according to the signal applied from the controller 385; an emitter common transistor 353 which becomes on when the signal outputted from the latch 351 is applied to its base and becomes off when the signal is not applied to its base; and a resistor 352 which is connected to the collector of the emitter common transistor 353 and drops the reference voltage(Vcc). At this time, the emitter common transistor 353 in which the resistor 352 is connected to its collector is plural.

Also, the A/D converting unit 360, as shown in FIG. 5B, of the ultrasonic receiving means 300, includes: a bridge circuit 371 which consists of three diodes 362, 367, 364 and half-wave rectifies the sinusoidal signal outputted from the second OP-AMP of the ultrasonic receiving signal detector 340; a capacitor 368 which detects the peak of the half-wave rectified signal outputted from the bridge circuit 371; a resistor 367 which forms a current discharging loop to shorten the discharging time when the discharging time of the capacitor 368 becomes long due to a large input impedance of the A/D converter 369; the zener diode 365 which generates the zener voltage according to the DC voltage produced by the bridge circuit 371 and the capacitor 368; and A/D converter 369.

Also, the key input unit 400, as shown in FIG. 5C, of the ultrasonic receiving means 300, includes: a down switch 411; an up switch 412; a manual/fuzzy mode selecting switch 413; resistors 408–410 which are connected to said switches respectively and drops the reference voltage applied to said switches; a resistor 407 which drops the reference voltage(Vcc) and applies the dropped voltage of the reference voltage(Vcc) to the INTO of the controller 385; and diodes 401–403 and capacitors 404–406 that form a loop through which the dropped reference voltage(Vcc) is applied to the controller 385 in the case that one of said switches is not selected, and that stabilize the dropped voltage of the reference voltage (Vcc).

Also, the controller 385, as shown in FIG. 5D, of the ultrasonic receiving means 300, includes: a CPU 386 which outputs signals according to the signal applied from the key input unit 400 and outputs signal to the sound generator 380 and a LCD 480 according to the A/D converting unit 360 if the output signal of the power supply 450 is applied; a ROM 387 which stores execution programs that are executed according to the signal applied from the CPU 386; a RAM 388 which stores data of the program executed in the ROM 387 on the address appointed by the CPU 386; and an IC chip selector 389 which selects an IC chip to read and write the data on the address appointed by the CPU 386.

Also, the LCD 480, as shown in FIG. 5D, of the ultrasonic receiving means 300, is a liquid crystal display device which displays data signals applied from the ultrasonic received signal detector 340, the A/D converting unit 360 and the controller 385, and comprises of: a data driver 481, a LCD RAM 482, a LCD driver 483, and a LCD module 484.

Also, the sound generator 340 includes a speaker which generates sound signals such as 'pi-' according to the signal applied from the controller 385.

The operation of the sealing quality tester and its controlling method of the car of the invention is specified with reference to FIG. 3 to FIG. 6.

Firstly, an examiner who examines the sealing quality of the car installs the ultrasonic transmitting means 100 inside the car, connects the battery 111 to the cigar lighter jack of the car, and positions the ultrasonic transmitting sensors 183–186 at the position where the sealing quality is suspicious or at a predetermined position to examine the sealing quality. The examiner, then, turns on the power switch 113.

At this time, plural ultrasonic sensors 183–186 are used to radiate the ultrasonic wave in every direction.

Thus, power is supplied to the parts of the ultrasonic transmitting means 100 through the connection of the battery 111 to the cigar lighter jack.

The battery 111 can be connected not only to the cigar lighter jack but to the terminal of another power supply according to the surroundings in which the inspection of the sealing quality test is executed.

At this time, the supplementary power supply 112 is charged by the predetermined voltage which is the dropped voltage applied through battery by a resistor 119, and if the supplementary power supply 112 is fully charged, the ultrasonic transmitting means 100 can be operated by the supplementary power supply 112. The capacitor 114 stabilizes the power applied from the battery 111 and the supplementary power supply 112.

If the reference voltage (Vcc) of the power supply 110 is applied to the charge detector 130, the zener diode 135 is reverse biased by the dropped voltage due to the resistor 132, and thus, the zener diode 135 generates the zener voltage. The zener voltage is applied to the noninverting terminal of the comparator 131 and at the same time, the dropped voltage of the reference voltage due to the resistor 133 and 134 is applied to the inverting terminal of the comparator 131. Thus, the comparator 131 compares the two inputs from the inverting and the noninverting terminals.

If the zener voltage applied and the voltage of the resistor 134 are equal, the comparator 131 outputs low signal. Thus, the low voltage is applied to the resistor 137 and the current does not flow to the LED 139. Therefore, the examiner of the sealing quality of the car can recognize that the ultrasonic transmitting means 100 is fully charged because of the LED 138 is light-emitting.

When the examiner cannot use the battery 111, he can operates the ultrasonic transmitting means 100 by using the supplementary power supply 112.

In this case, the supplementary power supply 112 acts in the same way as the battery 111. Furthermore, if the supplementary power supply 112 is used for long time, the zener voltage of the zener diode 135 is not generated. Thus, low signal is input to the non inverting terminal of the comparator 131.

Thus, the comparator 131 compares the dropped voltage of the reference voltage by the resistors 133, 134 and the low signal applied from the zener diode 135, and if the two signals—that is, the dropped voltage and the low signal— are not equal the comparator outputs the high signal. Thus, the examiner can find out that the supplementary power supply 112 is discharged by LED 139' light-emission.

On the other hand, if the reference voltage(Vcc) is applied from the power supply 110 to the electrode which is placed at the both ends of the crystal oscillator 161 of the ultrasonic oscillator 160, the crystal oscillator 161 oscillates about 4 MHz signal. At this time, the power applied to the crystal oscillator 161 is stabilized by the CMOS invertor 162 and the feedback resistor 166.

Also, the correct oscillation of the 4 Mhz signal is achieved by regulating the variable capacitor 163 and by the capacitor 164 blocking the harmonic signal components oscillated in the crystal oscillator 161.

The 4 MHz signal oscillated in the crystal oscillator 161 is applied to the frequency divider 165 and is frequency-divided by a hundredth ratio. The frequency-divided 40 KHz signal is then applied to the CMOS invertors 171–174 of the ultrasonic generator 170. The CMOS invertors 171–174 act as buffers between the ultrasonic oscillator 160 and the ultrasonic generation sensors 183–186.

The signal applied to the CMOS invertors 171–174 is applied to the both ends of each ultrasonic generation sensors 183–186 through each pair of the serially coupled CMOS invertors 175, 179, 176, 180, 177, 181 and 178, 182. Thus, the ultrasonic generation sensors 183–186 generate the ultrasonic waves.

On the other hand, the operation to the ultrasonic receiving means 300 is specified in details with reference to FIG. 5.

Firstly, an examiner who examines the sealing quality of the car connects the battery terminal of the power supply 450 with the battery of the car or other power supply terminal and turns on the power switch 453. Then, the reference voltage(Vcc) is applied to the parts of the ultrasonic receiving means 300.

The diode 451 blocks the voltage applied to the circuits when the polarity of the battery 111' applied to circuits is altered and the capacitor 452 stabilizes the voltage applied from the battery.

If the power switch 453 becomes on, the transistor 459 also becomes on because the dropped voltage of the reference voltage( Vcc) by the resistors 454, 456—that is, the voltage of the resistor 456—is applied to its base, and thus, the transistor 461 becomes on because 0 V is applied to its base.

Thus, the reference voltage(Vcc) is outputted because the power of the battery 111' is inputted to the electrostatic voltage IC 463. At this time the capacitors 462 and 464 stabilizes the voltages induced between the nodes where each capacitor is inserted.

The reference voltage(Vcc) is applied to the controller 385, and thus, the controller 385 applies a signal to the base of the transistor 459 through the diode 465. The transistor 459 becomes on and thus, the reference voltage(Vcc) output become continuous.

On the other hand, if the power switch is pushed once more, the voltage of the resistor 456 is applied to the controller through the diode 466.

If the voltage signal is applied to the controller 385, the transistor 459 becomes off because the controller 385 interrupts the output of the signal to diode 465. Thus, the reference voltage is not outputted from the power supply 450.

On the other hand, if the reference voltage is applied from the power supply 450, the ultrasonic receiving sensor 311 of the ultrasonic receiver 310 detects the ultrasonic signals which leak out from the fine holes or chasms formed in the inside of the car and applied the received ultrasonic signals to the high pass filter 314.

The high pass filter 314 consists of the resistor 313 and capacitor 315 as shown in FIG. 5B. The high pass filter 314 filters the audio frequency signal of 10–2000 Hz and other signals below 40 Khz.

The signals which pass through the high pass filter 314 is inputted to the inverting terminal of the first OP-AMP 341 and also, the dropped voltage of the reference voltage(Vcc) by the resistors 343, 344, that is, the voltage of the resistor 344 is applied to the noninverting terminal of the first OP-AMP 341. The first OP-AMP amplifies the difference of the two input voltage and outputs the amplified voltage. At this time, the amplifying ratio of the first OP-AMP 341 is determined by the ratio of the resistors 342 and 315.

The signal output from the first OP-AMP 341 is inputted to the inverting terminal of the second OP-AMP 348 through the DC blocking capacitor 345 and the resistor 346 and also, the dropped voltage of the reference voltage(Vcc) by the resistors 345, 346 is inputted to the noninverting terminal of the second OP-AMP 348. And thus, the second OP-AMP amplifies the difference of the two input voltages. At this time, the amplifying ratio of the second OP-AMP 348 is determined by the ratio of the resistance of the resistors 373 and 346.

The sinusoidal signal amplified in the second OP-AMP 348 is a half-wave rectified by the diodes 362, 376, 364 of the A/D converting unit 360.

Thereafter, the peak of the half-wave rectified signal is detected by the capacitor 368 and the zener diode 365 is reverse biased by the detected peak such that the zener diode 365 generates the zener voltage. The generated zener voltage is applied to the A/D converter 369. At this time, the loop to discharge the capacitor 368 quickly is formed by the resistor 367. The signal output from the A/D converter 369 is applied to the controller 385.

On the other hand, if the examiner who examines the sealing quality of the car wants to regulate the sensitivity and the multiplying ratio for the detected ultrasonic signals, he turns on the up switch 412 of the key selecting unit 400. Then, the reference voltage(Vcc) is applied to the controller 385 through the resistor 400 and thus, the controller 385 outputs the signal to the latch 351 of the latch unit 350 according to the applied signal. Thus, the latch 351 outputs the signal to one of the output lines and the transistor 353 becomes on when the output signal is inputted to the base of the transistor 353.

If the transistor 353 becomes on, the reference voltage (Vcc) is applied to the resistor 352 and the current passing through the resistor 352 flows to the ground through the emitter of transistor 353.

If, however, the transistor 353 becomes off, the current flows to resistor 373 through the analog switch 349 and thus, the voltage of the resistor 373 is applied to the noninverting terminal of the second OP-AMP 348.

On the other hand, another plural transistor(depicted as dots and 353'–353'" in the FIG. 5B) and the same number of another analog switches 349–349'" as that of said transistors operate in the same way as the transistor 353 and the analog switch 349 operate according to the signal output from the latch 351.

Thus, if the voltage signal is inputted to the inverting terminal of the second OP-AMP 348, the ultrasonic signal is amplified by the ratio of resistance of the resistor 346 and one of the resistors 373–373'" which is connected to one of said another analog switches 349–349'" respectively. At this time, since the number of the transistor such as the transistor 353 and the number of the analog switch such as the analog switch 349 are plural and also, the number of the resistor with different resistance such as the resistor 373 are plural, the multiplying ratio according to the ratio of the resistor 346 and one of the respective different resistors 373 . . . 373"" is determined by realizing the selection of the output of the latch 351 according to the signal of the key input unit 400 at the controller 385. At this time, the resistors 352–352'" and 354–354'" are resistors for voltages down and their respective number is the same as the transistors 353–353'" and the analog switches 349–349'" .

Also, if it is required to lower the multiplying ratio, the down switch 411 is turned on and thus, the multiplying ratio of the ultrasonic signal is decreased like the case that the up switch 412 becomes on.

Furthermore, the operation of the key input unit 400 is as follows:

If the reference voltage(Vcc) is applied, the high signal is applied to the ports(1.4, 1.3, 1.2, 1.0) of the controller 385 and the low signal is inputted to the interrupt(INTO).

At this time, if the down switch 411 becomes on, the low signal is applied to the port 1.4 and at the same time, the high signal is inputted to the interrupt INTO and thus, the predetermined multiplying ratio decreasing operation is executed by the controller 385.

The controlling method of the sealing quality tester of the car of the invention is specified in detail with reference to FIG. 2 to FIG. 6.

Figure 6A:
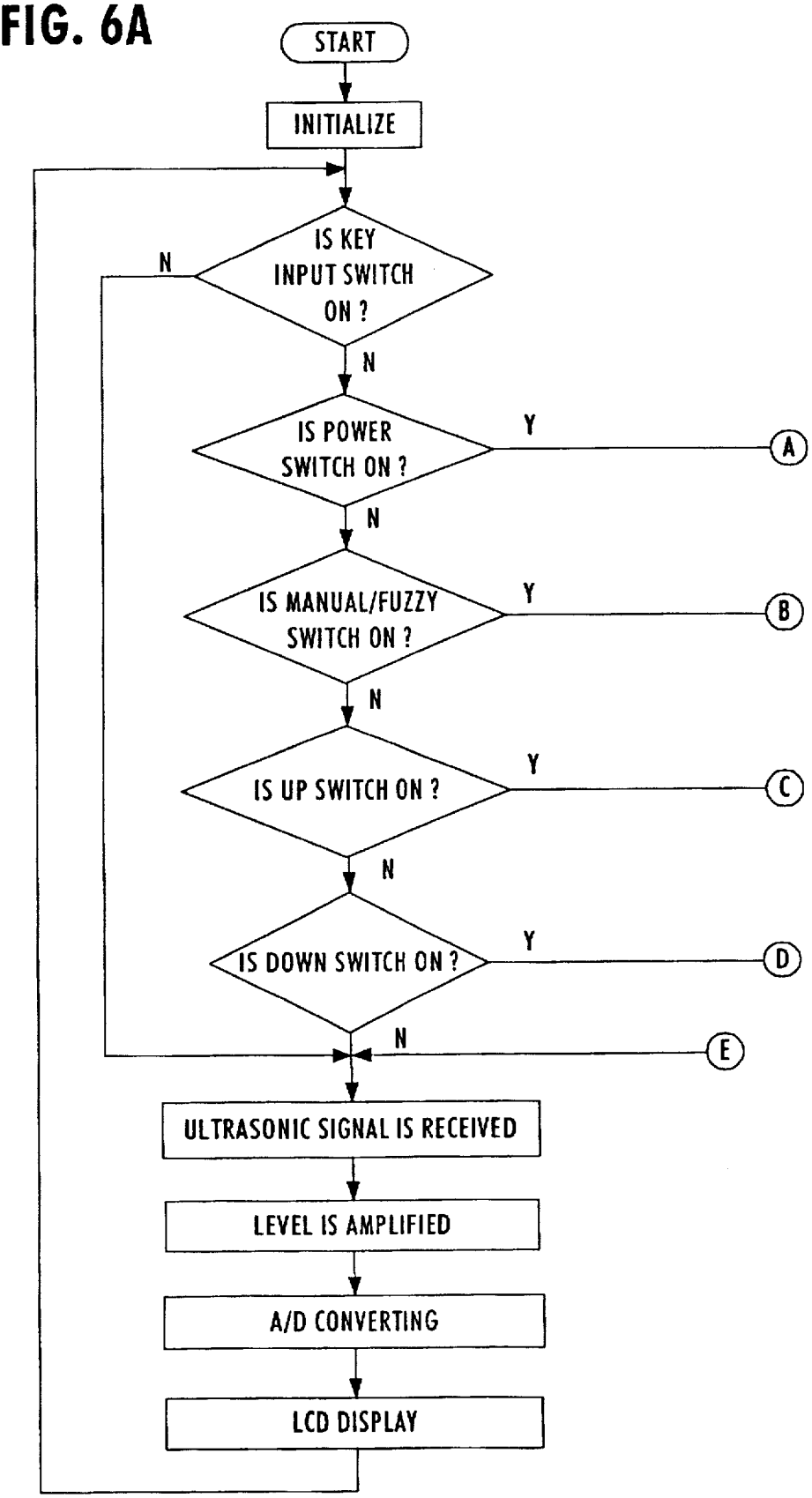
FIG. 6A and 6B is a flowchart showing the controlling method of the sealing quality detector of the invention.
Figure 6B:
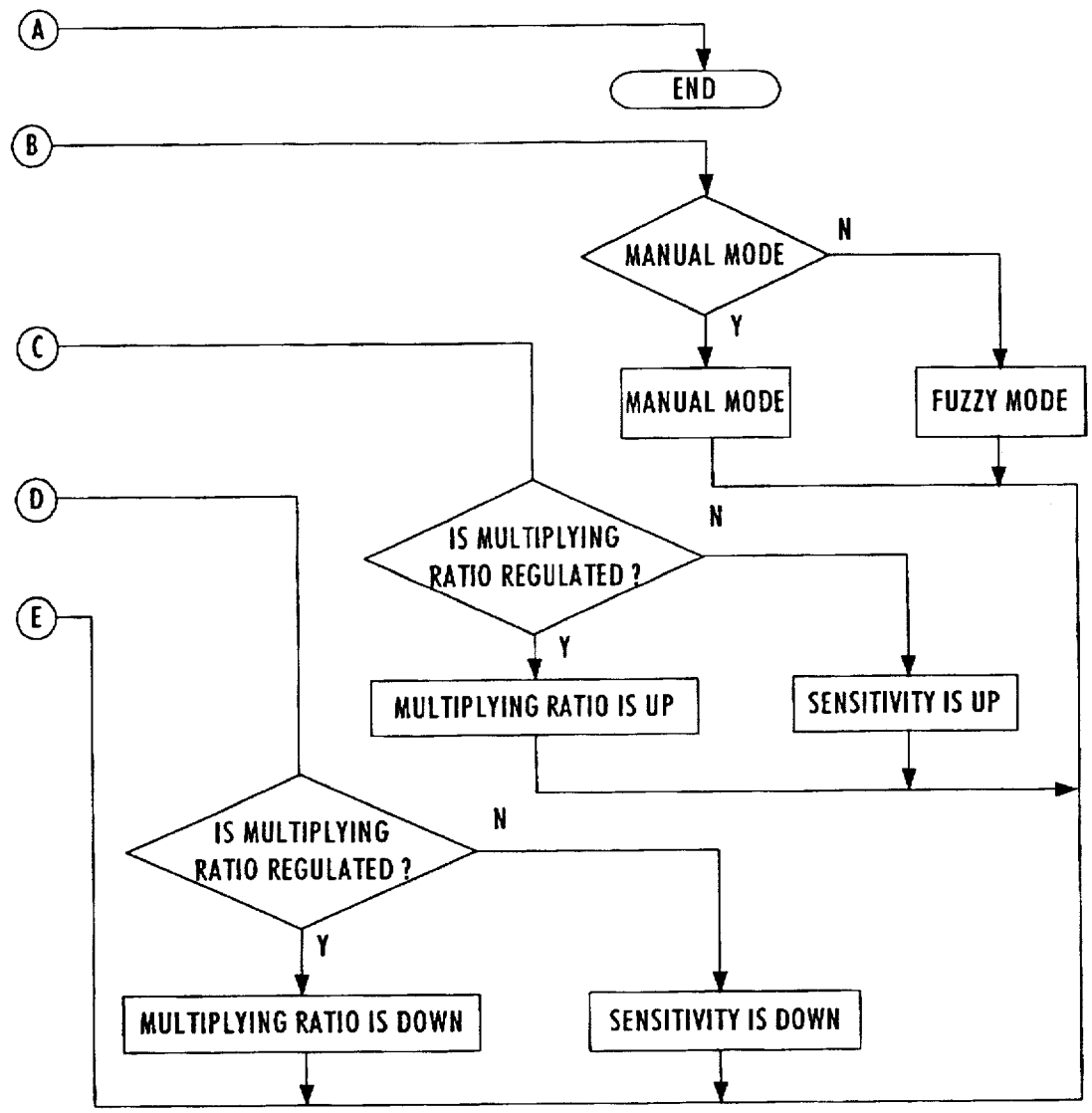

Firstly, the controlling method, as shown in FIG. 6, of the sealing quality tester includes: the up or down switch 411 or 412 selecting step to regulate the multiplying ratio and the sensitivity of the ultrasonic signals received in the ultrasonic signal receiver 310; the manual/ fuzzy mode selecting step to regulate the multiplying ratio and the sensitivity of the ultrasonic signals received in the ultrasonic signal receiver 310 according to the selecting of the up or down switch 411 or 412 in the up or down switch 411 or 412 selecting step manually or fuzzily; the multiplying ratio and the sensitivity increasing step to increase the multiplying ratio and the sensitivity of the ultrasonic signals received in the ultrasonic signal receiver 310 according to the selecting of the up switch 411 in the up or down switch 411 or 412 selecting step; the multiplying ratio and the sensitivity decreasing step to decrease the multiplying ratio and the sensitivity of the ultrasonic signals received in the ultrasonic signal receiver 310 according to the selecting of the down switch 412 in the up or down switch 411 or 412 selecting step; and the displaying step to display the multiplying ratio and the sensitivity regulated signal according to the selecting of the up or down switch 411 or 412 in the up or down switch 411 or 412 selecting step on the LCD 480 and the sound generator 380. Reference numbers 1–4 of FIG. 2 designate the respective ultrasonic generator sensors corresponding to ultrasonic generation sensors 138–186 of FIG. 4 and reference numbers 9 and 10 designate the menu switch that corresponds to the manual/fuzzy mode selecting switch 413 of FIG. 5C and power switch that corresponds to the switch 453 of FIG. 5A.

The controlling method of the sealing quality tester of the car which includes the steps as described above is specified more in detail in the following:

Firstly, an examiner who examines the sealing quality of the car installs the ultrasonic transmitting means 100 of the sealing quality tester of the car of the invention in the inside of the car and connects battery 111 and positions the ultrasonic transmitting sensors 183–186 at the suspicious position about the sealing quality or at the predetermined position to examine the sealing quality and then, turns on the power switch 113. At this time, the connection of battery 111 is realized by the connection of the cigar lighter jack.

Thereafter, the car is sealed up by closing the components such as the door and windows.

A connection wire jack is, then, connected to the battery jack coupler 5 and the power switch 453 turns on.

The various parts of the sealing quality tester of the car of the invention are operated.

In the state that the sealing quality tester of the car of the invention is operated, the sealing quality of the car is inspected by positioning the ultrasonic signal receiving sensor 311 to the place where sealing quality of the car is suspicious or the place where the sealing quality of the car is generally inspected.

The detected ultrasonic signals are processed in the ultrasonic receiving means 300 of the sealing quality tester of the car of the invention and then, any desired display is displayed in the sound generator 380 and LCD 480.

At first, if the power is applied to the sealing quality tester of the car of the invention, the controller 385 estimates the operation mode is manual mode or fuzzy mode.

If the examiner wants to increase or decrease the sensitivity and the multiplying ratio of the received ultrasonic signals, the up or down switch is selected by pushing the up or down switch button 7, 8. For example, if the up switch button 7, that is, up switch 411 is selected, the sensitivity and multiplying ratio of the received ultrasonic signals are increased by the controller 385.

The regulation of the sensitivity and multiplying ratio of the received ultrasonic signals is finished and then, the examiner can confirm the sealing quality of the car by the display of the LCD 480 and the sound of the sound generator 380 which operate according to the received and regulated ultrasonic signals.

According to the sealing quality tester and its controlling method of the car of the invention, any inconvenience that we experience in rainy day such as water leakage and the possibility of traffic accidents can be reduced because any holes and chasms which are formed in the inside of the car that are normally difficult to detect can be detected easily and quickly by this invention.

And also, the cost that the owner of the car should pay on repairing the car is reduced greatly and the time that is required in the construction process of the car is reduced to one tenth extent.

It will be apparent, of course, that many modifications may be made in the above-described embodiments without departing from the scope of the invention, which is defined by the claims below.

What is claimed is:

1. A sealing quality tester of the car including:
   a separate ultrasonic transmitting means comprising a power supply, a charge detector for a supplementary power supply, an ultrasonic oscillator and an ultrasonic generator; and
   a separate ultrasonic receiving means comprising an ultrasonic receiver, an ultrasonic signal detector, an A/D converting unit, a controller, a power supply, a key input unit, a sound generator and a liquid crystal display
   wherein the ultrasonic oscillator in said ultrasonic transmitting means includes: a crystal oscillator which oscillates by 4 MHz when the voltage is applied to both ends of its electrode; a CMOS inverter which amplifies the reference voltage and applied to the crystal oscillator to the desired extent; a variable capacitor which regulates the oscillation frequency from the crystal oscillator; a blocking capacitor which blocks the harmonic components oscillated from the crystal oscillator; and a frequency divider which divides the oscillation frequency of the signal from the crystal oscillator by a hundredth ratio.

* * * * *